United States Patent [19]

Kramer et al.

[11] 4,288,454
[45] Sep. 8, 1981

[54] ANTIVIRAL 1-ADAMANTYL-3-(PHENYLSULFONYL)-THIOUREAS

[75] Inventors: Michael J. Kramer, Glen Ridge; Jefferson W. Tilley, North Caldwell, both of N.J.

[73] Assignee: Hoffman-La Roche Inc., Nutley, N.J.

[21] Appl. No.: 103,138

[22] Filed: Dec. 13, 1979

Related U.S. Application Data

[63] Continuation of Ser. No. 927,072, Jul. 24, 1978, abandoned.

[51] Int. Cl.³ .................... A01N 41/06; C07C 143/82; C07C 143/833; C07C 133/06
[52] U.S. Cl. ..................................... 424/321; 564/23
[58] Field of Search ............... 260/397.7 D, 552 R, 260/553 D, 553 DA; 424/321; 564/23

[56] References Cited

U.S. PATENT DOCUMENTS

| | | | |
|---|---|---|---|
| 3,096,372 | 7/1963 | Gerzon | 260/553 D |
| 3,214,467 | 10/1965 | Haack et al. | 260/552 R X |
| 3,259,544 | 7/1966 | Wright | 260/553 D X |
| 3,409,644 | 11/1968 | Muller et al. | 260/552 R X |
| 3,450,721 | 6/1969 | Dietrich | 260/553 D X |
| 3,504,026 | 3/1970 | Aumuller et al. | 260/552 R X |
| 3,547,954 | 12/1970 | Dietrich | 260/552 R X |
| 3,557,163 | 1/1971 | Dietrich | 260/552 R X |
| 3,773,802 | 11/1973 | Zschocke et al. | 260/552 R X |
| 3,780,101 | 12/1973 | Bretschneider et al. | 260/553 D |
| 3,843,661 | 10/1974 | Weber et al. | 260/552 R X |

FOREIGN PATENT DOCUMENTS

| | | | |
|---|---|---|---|
| 215920 | 6/1956 | Australia | 260/553 D |
| 732230 | 4/1966 | Canada | 260/553 D |
| 1434499 | 2/1966 | France | 260/553 D |
| 1434500 | 2/1966 | France | 260/553 D |
| 4001M | 4/1966 | France | 260/553 D |

OTHER PUBLICATIONS

Geigy A.G., CA 62: 16134d (1965).

Primary Examiner—Winston A. Douglas
Assistant Examiner—Raymond K. Covington
Attorney, Agent, or Firm—Jon S. Saxe; Bernard S. Leon; James H. Callwood

[57] ABSTRACT

The present invention relates to 1-adamantyl-3-(phenylsulfonyl)thioureas of the formula

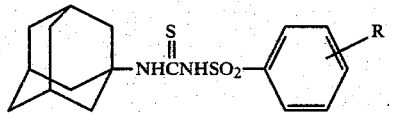

wherein R is lower alkyl, amino or lower alkanoylamino to methods of preparation thereof and to their use in the treatment and prevention of viral infections in mammalian and avian hosts.

4 Claims, No Drawings

ANTIVIRAL 1-ADAMANTYL-3-(PHENYLSULFONYL)THIOUREAS

This is a continuation of application Ser. No. 927,072, filed July 24, 1978, now abandoned.

BACKGROUND OF THE INVENTION

Amantadine hydrochloride (1-adamantanamine hydrochloride), which is considered to be the most important agent presently available for the prevention and treatment of viral infections caused by influenza type A viruses, exhibits serious central nervous system (CNS) side effects, such as inability to concentrate, nervousness and insomnia, and drowsiness in the host. While these CNS effects are not the sole cause of the commercial failure of the drug (and the subsequent decrease in research and development activity in the area of antivirals), they have significantly contributed to the general non-acceptance of amantadine hydrochloride by the medical profession. Thus, there is a need for an antiviral agent exhibiting prophylactic and therapeutic activity similar to that of amantadine without the CNS effects associated with this first generation drug to not only provide physicians with an alternative to or conjunctive with immunoprophylaxis, but also to stimulate further research in the prevention and treatment of viral infectious disease. See, for example, T. H. Maugh III, Science, 192, 128 (1976), G. G. Jackson and E. D. Stanley, J. Am. Med. Assoc. 235, 2739 (1976) and A. Chanin, J. Am. Med. Assoc., 237, (1977).

Providing an antiviral agent having a spectrum of activity closely related to that of amantadine free of CNS side effects would be a significant advance in the art.

DETAILED DESCRIPTION OF THE INVENTION

The present invention relates to antiviral 1-adamantyl-3-(phenylsulfonyl)thioureas, to methods of preparation thereof and to their use in the prevention and treatment of viral infectious disease in mammalian and avian hosts. More particularly, the present invention relates to antiviral 1-adamantyl-3-(phenylsulfonyl)thioureas of formula I

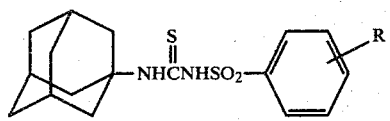

wherein R is lower alkyl, amino or lower alkanoylamino to methods of preparation thereof comprising condensing 1-adamantylamine of formula II

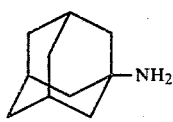

with phenylsulfonylisothiocyanates of formula III

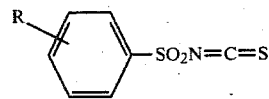

wherein R is lower alkyl or lower alkanoylamino to afford (phenylsulfonyl)thioureas of formula I wherein R is lower alkyl or lower alkanoylamino and hydrolyzing the lower alkanoylamino group of formula I to the corresponding amino function to yield (phenylsulfonyl)thioureas of formula I wherein R is amino, and to the prevention and treatment of mammalian and avian hosts afflicted with infectious disease without the elicitation of undesirable CNS side effects.

As used throughout the specification and appended claims the term "alkyl" refers to the residue formed by removal of a hydrogen atom from a straight or branched chain alkane having from 1 to 20 carbon atoms such as, for example, methyl, ethyl, 2-propyl, 2-methylpropyl, 2-methylbutyl, 3-methylpentyl, 3-ethylpentyl, 3-ethylhexyl and so forth. The term "alkanoyl" refers to the residue formed by removal of a hydroxyl moiety of the carboxyl group of a straight or branched chain alkanoic acid having 1 to 20 carbon atoms. Examples of "alkanoyl" groups include ethanoyl, propionyl, 2-methylpropionyl, 2-methylbutanoyl, 3-methylpentanoyl, 3-ethylpentanoyl, 3-ethylhexanoyl and so forth. The term "lower" as applied to any of the aforementioned groups refers to those groups having 1 to 8 carbon atoms. The term "alkali metal" refers to the elements lithium, sodium and potassium. The term "alkanol" refers to the compound formed by replacement of a proton of a straight or branched chain alkane having 1 to 20 carbon atoms with a hydroxyl moiety.

As hereinbeforementioned, the 1-adamantyl-3-(phenylsulfonyl)thioureas of formula I, wherein R is lower alkyl or lower alkanoylamino, of the present invention are prepared by condensing commercially available 1-adamantylamine (II) with a sulfonylisothiocyanate III in an aprotic solvent. Suitable aprotic solvents include aliphatic and aromatic hydrocarbons, such as hexane, isooctane, benzene, toluene, xylene and the like, halocarbons such as chloroform, dichloromethane, carbon tetrachloride, 1,1-dichloromethane, 1,2-dichloroethane and the like and ethers such as diethyl ether, dimethoxyethane, bis(2-methoxyethyl)ethane, tetrahydrofuran, tetrahydropyran and the like. Halocarbons are preferred. Dichloromethane is most preferred.

The condensation temperature is not narrowly critical. It is desirable, however, to perform the reaction at a temperature within the range of about −20° C. to about the boiling point of the aprotic solvent. A reaction temperature within the range of about 0° C. to about 40° C. is preferred. Most preferred is a reaction temperature of about 25° C.

While the molar ratio of isothiocyanate of formula III to 1-adamantylamine of formula I is also not narrowly critical, it is desirable to employ an excess of the isothiocyanate. An excess of about 1.1 to about 3 molar-equivalents of isothiocyanate of formula III to amine of formula I is preferred, an excess of about 1.5 molar-equivalents of III to I being most preferred.

4-Tolysulfonylisothiocyanate, the sulfonylisothiocyanate of formula III wherein R is 4-methyl, is prepared according to the method reported by R. Gompper and W. Hagele in Chem. Ber., 99, 2885 (1966).

The requisite substituted sulfonylisothiocyanates of formula III wherein R is lower alkyl or lower alkanoylamino may also be generated in situ and reacted with 1-adamantylamine (II) to form 1-adamantyl-3-(phenylsulfonyl)thioureas of formula I wherein R is lower alkyl or lower alkanoylamino. Thus, for example, to prepare a 1-adamantyl-3-(4-lower alkanoylaminophenylsulfonyl)thiourea of formula I wherein R is lower alkanoylamino, such as 1-adamantyl-3-(4-acetamidophenylsulfonyl)thiourea (I, wherein R is 4-acetamido), one treats an N-lower alkanoylaminosulfanilamide of formula V

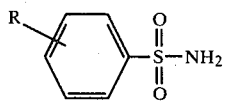

wherein R is lower alkanoylamino, such as $N^4$-acetylsulfanilamide (IV, wherein R is 4-acetamido) with carbon disulfide in the presence of an alkali metal hydroxide and an aqueous solvent to afford a dialkali metal salt of an N-lower alkanoylaminophenylsulfonyldithiocarbamate of the formula V

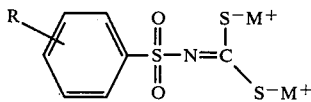

wherein R is lower alkanoylamino and M is alkali metal such as dipotassium 1-adamantyl-3-(4-acetamidophenylsulfonyl)dithiocarbamate (V, wherein R is 4-acetamido and M is potassium) which one then suspends in an aprotic solvent and treats with a solution of phosgene in an aromatic solvent to yield a solution of the aforementioned sulfonylisothiocyanates of formula III wherein R is lower alkanoylamino. Treatment of the resulting solution of sulfonylisothiocyanate of formula III, wherein R is lower alkanoylamino and aprotic-aromatic solvent combination with 1-adamantylamine (II) gives the desired 1-adamantyl-3-(4-lower alkanoylaminophenylsulfonyl)thioureas of formula I wherein R is lower alkanoylamino, such as 1-adamantyl-3-(4-acetamidophenylsulfonyl)thiourea (I, wherein R is 4-acetamido).

Suitable aqueous solvents for the first step in the in situ preparation of sulfonylisothiocyanates, i.e., the reaction of the sulfanilamide of formula IV wherein R is lower alkanoylamino with carbon disulfide, include water and water-alkanol mixtures, such as, for example, mixtures of water and methanol, ethanol, 2-propanol and the like.

Useful alkali metal hydroxides include lithium, sodium and potassium hydroxides.

As suitable aprotic and aromatic solvents for the second step, i.e., the reaction of the dialkali metal salt of a (phenylsulfonyl)dithiocarbamate of formula V with phosgene, in the in situ preparation of the requisite sulfonylisothiocyanates, there may be mentioned, respectively, aliphatic hydrocarbons such as pentane, hexane, isooctane and the like, halocarbons such as chloroform, methylene chloride, carbon tetrachloride and the like, and ethers such as dimethyl ether, diethyl ether, dimethoxyethane, tetrahydropyran and tetrahydrofuran and the like, and benzene, toluene, xylene and the like.

The temperature at which the reactions involving carbon disulfide and phosgene are carried out is not narrowly critical. However, due to the volatility of these reactants, it is preferred to conduct the reactions at temperatures below about 20° to about 25° C.

Similarly, while the relative amounts of the reactants are not narrowly critical, it is preferred to employ excess carbon disulfide and phosgene to compensate for volatility losses. Excesses of the order of about 1.2 to about 10 molar-equivalents of carbon disulfide and phosgene to sulfanilamide of formula IV wherein R is lower alkanoylamino are preferred.

To prepare 1-adamantyl-3-(phenylsulfonyl)thioureas of formula I wherein R is amino, the 1-adamantyl-3-(lower alkanoylaminosulfonyl)thioureas of formula I wherein R is lower alkanoylamino are hydrolyzed by alkali metal hydroxides in the presence of aqueous solvents. Aqueous solvents suitable for the hydrolysis reaction include water and mixtures of water and alkanols such as, for example, methanol, ethanol, 2-propanol and the like, and mixtures of water and ethers such as dimethoxyethane, tetrahydrofuran, dioxane and the like. As suitable alkali metal hydroxides there may be mentioned lithium, sodium and potassium hydroxides.

Notwithstanding the presence of several functional moieties susceptible to hydrolysis, the cleavage of the lower alkanoylamino group may be performed in the presence of excess alkali metal hydroxide and at elevated temperatures. Excesses of about 20 molar-equivalents are preferred, excesses of about 10 molar-equivalents being most preferred. Elevated temperatures of about 50° C. to about the reflux temperature of the reaction medium are preferred; elevated temperatures of about the reflux temperature of the reaction medium being most preferred.

The (phenylsulfonyl)thioureas of formula I of the present invention possess prophylactic and therapeutic antiviral activity without significant CNS effects and are thus useful for the prevention of viral infection of mammalian or avian hosts susceptible to viral infection and for the treatment of such hosts afflicted with viral infection when CNS effects are undesirable or contraindicated.

The intraperitoneal (ip) and oral (po) antiviral activity of the (phenylsulfonyl)thioureas of the present invention are demonstrated in mammals, such as mice, by infecting the animal with an influenza virus such as influenza A2/Asian/J305 and then administering the compounds dissolved or suspended in a suitable vehicle such as water, to the animal immediately before infection and at predetermined time intervals thereafter. In this test one-half of the virally infected mice survived for 21 days or longer after infection when treated with a 1-adamantyl-3-(aminophenylsulfonyl)thiourea of the present invention at a dose of about 16 mg/kg., i.e., the 1-adamantyl-3-(aminophenylsulfonyl)thioureas of the present invention exhibited a Protective Dose$_{50}$ (PD$_{50}$) of about 16 mg/kg. in the mouse. Of particular interest is 1-adamantyl-3-(4-aminophenylsulfonyl)thiourea, the PD$_{50}$s of which compared favorably with those of amantadine, and which, like amantadine, exhibited both prophylactic and therapeutic antiviral effects. While the ip and po PD$_{50}$s of amantadine were about 6 and about 4 mg/kg, respectively, in the mouse, those of 1-adamantyl-3-(4-aminophenylsulfonyl)thiourea were of the same order of magnitude, falling at about 16 mg/kg (ip) and about 35 mg/kg (po) in the same animal. At pre-infection doses of 50 and 200 mg/kg, amantadine and 1-adamantyl-3-(4-aminophenylsulfonyl)thiourea showed percent corrected survival values of 72 and 77, respectively. At 5 hour post-infection doses of 100 mg/kg and 200 mg/kg., amantadine and 1-adamantyl-3-(4-aminophenylsulfonyl)thiourea exhibited percent corrected survival values of 67 and 36, respectively. At 24 hour post-infection dosing, the percent corrected survival values for amantadine (100 mg/kg dose) and 1-adamantyl-3-(4-aminophenylsulfonyl)thiourea (200 mg/kg dose) were 77 and 36, respectively.

In addition to the aforedescribed in vivo antiviral activity, the (phenylsulfonyl)thioureas of the present invention show in vitro effects against (A2/Asian/J305) influenza virus as demonstrated in the tube dilution assay. To perform this assay, monolayers of Rhesus monkey kidney cells were infected with serial ten-fold dilutions of the influenza virus. The mean tissue culture infective doses ($TCID_{50}$) of the virus-infected cultures in the presence and absence of non-cytotoxic doses of the test substances were determined on the basis of hemadsorption after 4 days incubation at 37° C.

In the tube dilution assay, 1-adamantyl-3-(4-aminophenylsulfonyl)thiourea reduced the titer of influenza A2/Asian/J305 virus in Rhesus monkey kidney cells at 12.5 µg/ml. By comparison therewith, amantadine inhibited the growth of the virus at 0.05 µg/ml.

The acute toxicity and symptom profile of the (phenylsulfonyl)thioureas of the present invention as well as amantadine were determined in the mouse by administering the compound suspended in 5% gum acacia intraperitoneally (ip) or orally (po) to three Charles River mice of either sex weighing 17 to 25 g. The animals were observed for lethality and gross signs or symptoms throughout the 24-hour test period. Lethal dose$_{50}$ values ($LD_{50}$) based on total lethality occurring over the 24-hour period were calculated using the probit analysis method described by Miller and Tainter in Proc. Soc. Exp. Med., 57, 261 (1964).

In this test, the $LD_{50}$ of 1-adamantyl-3-(4-aminophenylsulfonyl)thiourea, the compound of formula I wherein R is amino, was determined to be greater than 1000 mg/kg (po) and about 775 mg/kg (ip). Amantadine, in comparison therewith, had po and ip $LD_{50}$s of 900 and 245 mg/kg, respectively, in the acute toxicity and symptom profile assay.

Additionally, and equally significantly, whereas oral administration of amantadine (900 mg/kg) produced increased motor activity, tremors, Straub reaction, hypersensitivity and mydriasis in addition to symptoms of depression, such as decreased motor activity, ataxia, loss of righting reflex and muscle relaxation in the mouse, oral administration of 1-adamantyl-3-(4-aminophenylsulfonyl)thiourea (through 1000 mg/kg) produced no signs or symptoms in this animal. Intraperitoneally, amantadine produced CNS effects at a dose of 245 mg/kg similar to those elicited by oral administration of 1000 mg/kg of the drug. 1-Adamantyl-3-(4-aminophenylsulfonyl)thiourea, however, produced only minor CNS effects when administered intraperitoneally at doses of 600 and 1000 mg/kg.

The compounds of the present invention, useful in the treatment and prevention of viral infections can be made up in the form of conventional pharmaceutical preparations; for example, the aforesaid compounds can be mixed with conventional organic or inorganic inert pharmaceutical carriers suitable for parenteral or enteral administration such as, for example, water, gelatin, lactose, starch, magnesium stearate, talc, vegetable oil, gums or the like. They can be administered in conventional pharmaceutical forms e.g., solid forms, for example, tablets, dragees, capsules, suppositories or the like; or in liquid forms, for example, suspensions or emulsions. Moreover, the pharmaceutical compositions containing compounds of this invention can be subjected to conventional pharmaceutical expedients such as sterilization, and can contain conventional pharmaceutical excipients such as preservatives, stabilizing agents, emulsifying agents, salts for the adjustment of osmotic pressure or buffers. The composition can also contain other therapeutically active materials.

A suitable pharmaceutical dosage unit can contain from about 10 to 50 mg. of 1-adamantyl-3-(4-phenylsulfonyl)thiourea of formula I. Suitable parenteral and oral dosage regimens in mammals comprise from 30 mg/kg to about 150 mg/kg per day. However, for any particular subject, the specific dosage regimen should be adjusted according to individual need and the professional judgment of the person administering or supervising the administration of the aforesaid compounds. It is to be understood that the dosages set forth herein are exemplary only and that they do not to any extent limit the scope or practice of this invention.

The following examples illustrate the present invention. The compounds described hereafter were characterized by standard methods including elemental analysis and infrared, nuclear magnetic resonance and mass spectroscopy. All temperatures are in degrees Centigrade.

EXAMPLE 1

1-Adamantyl-3-(4-acetamidophenylsulfonyl)thiourea. To a solution of 53.5 g. (0.24 mol) of $N^4$-acetylsulfanilamide in 200 ml. of dimethylformamide was added simultaneously a solution of 33 g. (0.50 mol) of potassium hydroxide in 50 ml. of water and 16.6 ml. (0.275 mol) of carbon disulfide over the course of 20 minutes while maintaining the reaction temperature below 20°. Upon completion of the addition, the mixture was stirred 1.5 hours and was diluted carefully with 1.5 liters of ethanol. The resulting precipitate was dried at 50° in vacuo and finally by suspension in 700 ml. of benzene and azeotropic distillation to remove the ethanol of crystallization.

The dipotassium salts so obtained were suspended in 500 ml. of methylene chloride in a 2 liter flask and 183 ml. of a 12.5% solution of phosgene in benzene was added such that the internal temperature did not rise above 25°. The suspension was allowed to warm to room temperature over 40 minutes, refluxed for 1.5 hour, diluted with an additional 500 ml. of methylene chloride and filtered hot. A total of 500 ml. of the solution were distilled and the residue was cooled as a solution of 20.42 g. (0.135 mol) of adamantylamine in 750 ml. of methylene chloride was added. The mixture was stirred overnight, filtered, and evaporated to 55.5 g. of a gum. Trituration with 500 ml. of ethanol then gave the (acetamidophenylsulfonyl)thiourea, 24.06 g. (44%), m.p. 176°–178°.

EXAMPLE 2

1-Adamantyl-3-(4-aminophenylsulfonyl)thiourea. A suspension of 28.25 g. (0.070 mol) of 1-adamantyl-3-(4-acetamidophenylsulfonyl)thiourea and 28 g. (0.70 mol) of sodium hydroxide in 500 ml. of water was refluxed for 1 hour. On cooling, the pH of the mixture was adjusted to 1 by dropwise addition of 6 N hydrochloric acid and the precipitate was recrystallized from methanol-water to give 20.8 g. (83%) of the (aminophenyl-sulfonyl)thiourea, m.p. 176°–179°.

EXAMPLE 3

1-Adamantyl-3-(4-methylphenylsulfonyl)thiourea.
To an ice cooled solution of 5.84 g. (0.0386 mol) of 1-aminoadamantine in 40 ml. of Spectro quality chloroform was added a solution of 12.36 g. (0.0580 mol) of 4-methylphenylsulfonylisothiocyanate (prepared according to R. Gompper and W. Hagele, Ber., 99, 2885 (1966) in 25 ml. of dry acetone. The resulting clear yellow reaction mixture was allowed to warm to room temperature overnight as the product slowly separated. Filtration gave 8.55 g. of 1-adamantyl-3-(4-methylphenylsulfonyl)thiourea, m.p. 170°–173° which on recrystallization from aqueous ethanol-dimethylformamide melted at 174°–176°.

We claim:

1. A method of treating a mammalian or avian host afflicted with a viral infection which comprises administering to the host an antivirally effective amount of an antiviral compound of the formula

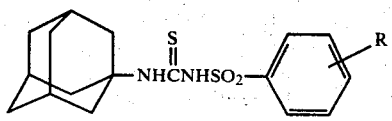

wherein R is amino.

2. The method of claim 1 wherein the antiviral compound administered to the mammalian or avian host is 1-adamantyl-3-(4-aminophenylsulfonyl)thiourea.

3. The method of claim 1 wherein the antiviral compound is administered to the mammalian or avian host in a dosage range of from about 16 to about 200 milligrams per kilogram of weight per day.

4. The method of claim 1 wherein the antiviral compound is administered orally to the mammalian or avian host.

* * * * *